United States Patent [19]

Nishimura et al.

[11] Patent Number: 4,845,279
[45] Date of Patent: Jul. 4, 1989

[54] METHOD OF PREPARING 4-TRIFLUOROMETHYL-2-NITROBENZOIC ACID AND NOVEL ISOMER

[75] Inventors: Yasunori Nishimura; Yoshihiko Gotoh, Kamifukuoka; Toshikazu Kawai, Kawagoe, all of Japan

[73] Assignee: Central Glass Company, Limited, Ube, Japan

[21] Appl. No.: 136,715

[22] Filed: Dec. 22, 1987

[30] Foreign Application Priority Data

Dec. 23, 1986 [JP] Japan .................................. 61-305277

[51] Int. Cl.$^4$ ............................................. C07C 79/46
[52] U.S. Cl. .................................... 562/438; 562/420; 562/422
[58] Field of Search ................. 562/438, 434, 420, 422

[56] References Cited

U.S. PATENT DOCUMENTS 3,703,546  11/1972  Leaper ................................. 562/438
3,910,995  10/1975  Gelfand ............................... 562/438
4,288,615   9/1981  Bright ................................. 562/434

OTHER PUBLICATIONS

Chem. Abstr., vol. 64, 3487f (3486h–3488d), 1966.
Chem. Abstr., vol. 49, 3897b (3896g–3998c), 1955.

*Primary Examiner*—Michael L. Shippen
*Attorney, Agent, or Firm*—Fleit, Jacobson, Cohn & Price

[57] ABSTRACT

An isomer mixture of 4-trifluoromethyl-2-nitrobenzoic acid and 4-trifluoromethyl-3-nitrobenzoic acid, which is a novel compound, is obtained by nitrating a compound represented by

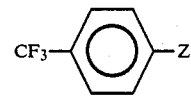

(Z is COY or CY$_3$, and Y is a halogen atom) with a nitrating agent comprising nitric acid and simultaneously hydrolyzing the radical Z. Each of the two isomers is easily isolated by treating the mixture with a basic neutralizing agent to obtain a solution containing the 2-nitro isomer and a precipitate containing the 3-nitro isomer.

7 Claims, No Drawings

METHOD OF PREPARING 4-TRIFLUOROMETHYL-2-NITROBENZOIC ACID AND NOVEL ISOMER

BACKGROUND OF THE INVENTION

This invention relates to a method of preparing 4-trifluormethyl-2-nitrobenzoic acid and a novel isomer, viz., 4-trifluoromethyl-3-nitrobenzoic acid.

4-Trifluoromethyl-2-nitrobenzoic acid (abbreviated to 4-TFM-2-NBA) is a compound useful as an intermediate material of some medicines, agricultural chemicals and liquid crystals, and the novel isomer too will be useful for similar purposes.

It is known to obtain 4-TFM-2-NBA by the steps of first converting 4-trifluoromethyl-2-nitroaniline into 4-trifluoromethyl-2-nitrobenzonitrile by Sandmeyer reaction and then hydrolyzing the nitrile (Chem. Abstr., 49, 3897b (1955)). The product of this process is fairly high in purity as indicated by the reported melting point of 140°–140.5° C. However, this process is not suitable for industrial practice because of involving problems such as difficulty of industrially preparing the starting material, 4-trifluoromethyl-2-nitroaniline, use of a very toxic cyanide in the essential Sandmeyer reaction and complicatedness of the operations.

Another known method for preparing 4-TFM-2-NBA is nitrating 4-trifluoromethylbenzoic acid (Chem. Abstr., 64, 3487f (1966)). However, the product of this method must be low in purity since the reported melting point of the reaction product, 109°–111° C., differs considerably from the aforementioned melting point.

SUMMARY OF THE INVENTION

It is an object of the present invention to provide an advantageous and industrially practicable method for preparing 4-TFM-2-NBA.

It is another object of the invention to provide a novel isomer of 4-TFM-2-NBA.

According to the invention there is provided a method of preparing 4-TFM-2-NBA, comprising the steps of nitrating a benzotrifluoride derivative represented by the general formula (1),

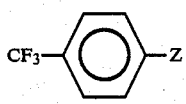

wherein Z represents COY or CY$_3$, and Y represents a halogen atoms, with a nitrating agent comprising nitric acid and simultaneously hydrolyzing the radical Z of the benzotrifluoride derivative to thereby obtain a mixture comprising 4-trifluoromethyl-2-nitrobenzoic acid and 4-trifluoromethyl-3-nitrobenzoic acid (4-TFM-3-NBA), treating the mixture with a basic neutralizing agent so as to obtain a solution containing 4-TFM-2-NBA and a precipitate containing 4-TFM-3-NBA, and isolating 4-TFM-2-NBA from the solution and 4-TFM-3-NBA from the precipitate.

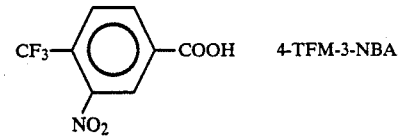

4-TFM-3-NBA obtained by this method is a novel compound. In 4-TFM-2-NBA and 4-TFM-3-NBA, both nitro group and carboxylic group are functional groups high in reactivity. Accordingly both 4-TFM-2-NBA and 4-TFM-3-NBA serve as intermediate materials for synthesizing various fluorine-containing aromatic compounds including ones useful as medicines, agricultural chemicals or liquid crystals.

The starting material for the method according to the invention, a benzotrifluoride derivative of the general formula (1), is readily available as an industrial material. By nitrating the starting compound with nitric acid or a mixed acid of nitric acid and sulfuric acid the radical Z of the starting compound is simultaneously hydrolyzed into carboxylic group. That is, the aimed nitro-compounds are formed very easily. The nitrating and hydrolyzing reaction gives an isomer mixture of 4-TFM-2-NBA and 4-TFM-3-NBA in which the proprtion of 4-TFM-2-NBA to 4-TFM-3-NBA is about 2:1, and each of these two isomers can easily be isolated by partial neutralization treatment of the mixture. Accordingly the method of the invention is very suitable and favorable for industrial application.

DETAILED DESCRIPTION OF THE INVENTION

In the practice of the present invention the nitrating agent is concentrated nitric acid or fuming nitric acid, or a mixed acid of concentrated or fuming nitric acid and concentrated sulfuric acid or fuming sulfuric acid. It is suitable to use 0.9 to 5.0 mols, and preferably 0.9 to 2.5 mols, of nitric acid per mol of the starting compound represented by the general formula (1). The reaction to nitrate the starting compound and hydrolyze its radical Z is carried out usually at a temperature in the range from room temperature to about 150° C., and preferably at a temperature in the range from 40 to 100° C. The reaction time is from about 1 hr to several hours.

After the above reaction the reaction liquid is diluted with water to thereby precipitate the reaction product containing both 4-TFM-2-NBA and 4-TFM-3-NBA, and the precipitate is partially neutralized by using a basic compound as a neutralizing agent. In practice the neutralizing agent is selected from hydroxides, carbonates and hydrogen carbonates of alkali metals or alkaline earth metals. Typical examples are NaOH, KOH, Ca(OH)$_2$, Na$_2$CO$_3$, K$_2$CO$_3$, NaHCO$_3$ and KHCO$_3$. It is possible to selectively dissolve 4-TFM-2-NBA by using a suitable quantity of such a neutralizing agent, which is not more than equimolar to 4-TFM-2-NBA existing in the treated precipitate. After separating 4-TFM-3-NBA which is in solid phase, the method liquid is render strongly acidic to thereby precipitate 4-TFM-2-NBA.

The invention is further illustrated by the following nonlimitative examples.

EXAMPLE 1

A resin-lined reactor having a capacity of 200 liters was charged with 100 kg of concentrated sulfuric acid and 12.5 kg of 98% fuming nitric acid, and 10 kg of 4-trifluoromethylbenzoyl chloride was gradually put into the mixed acid while maintaining the liquid temperature at 40°–60° C. Then, nitration reaction was carried out at 60° C. for 3 hr.

After the above reaction the reaction liquid was put into 120 liters of iced water to precipitate the reaction product. The precipitate was separated by filtration and put into 18 liters of water containing 1.05 kg of $Na_2CO_3$, and stirring was made for 30 min. After that an undissolved portion of the precipitate was separated by filtration and dried to thereby obtain 2.3 kg of 4-TFM-3-NBA. The mother liquor was rendered acidic by addition of 8 kg of concentrated hydrochloric acid, and a resultant precipitate was recovered by filtration and refined by recrystallization using 20 kg of chloroform. As the result 6.3 kg of 4-TFM-2-NBA of 99.9% purity (m.p. 140.5° C.) was obtained. The total yield of 4-TFM-2-NBA and 4-TFM-3-NBA was 76.3%.

Analysis of the obtained 4-TFM-3-NBA gave the following data.

Melting point: 169° C.

$^{19}F$-NMR (standard substance was $CF_3CO_2H$, in $CDCl_3$): $-15.5$ ppm (3F, s).

$^{1}H$-NMR (standard substance was TMS, in $CDCl_3$): 8.1–8.5δ(3H, m); 9.9δ(1H, s).

IR (KBr pellet): 2510–31310 cm$^{-1}$, 921 cm$^{-1}$ (γOH); 1730 cm$^{-1}$ (γC=O); 1562 cm$^{-1}$, 1375 cm$^{-1}$(γNO$_2$).

EXAMPLE 2

A glass reactor (capacity 100 ml) was charged with 128 g of 30% fuming sulfuric acid and 9.0 g of 4-trifluoromethylbenzotrichloride, and 12.8 g of conc. nitric acid (ca. 65–68%) was dropped into the reactor while the liquid temperature was maintained at about 50° C. Then, nitration reaction was carried out at 60° C. for 2 hr. After that the reaction liquid was put into 100 ml of iced water to precipitate the reaction product. The preciptiate was separated by filtration and put into 20 ml of water containing 0.3 g of NaOH, and stirring was made for 30 min. After that an undissolved portion of the precipitate was separation by filtration and dried to thereby obtain 2.1 g of 4-TFM-3-NBA. The mother liquor was rendered acidic by addition of 1.8 g of sulfuric acid, and a resultant precipitate was recovered by filtration and refined by recrystallization using 12 g of chloroform. As the result 4.0 g of 4-TFM-2-NBA was obtained. The total yield of 4-TFM-2-NBA and 4-TFM-3-NBA was 75.9%. Analysis of 4-TFM-3-NBA obtained in this example gave the same results as in Example 1.

EXAMPLE 3

A glass reactor having a capacity of 100 ml was charged with 98 g of concentrated sulfuric acid and 10.0 g of 98% fuming nitric acid, and 12.0 g of 4-trifluoromethylbenzoyl bromide was dropped into the reactor while maintaining the liquid temperature at about 50° C. Then nitration reaction was carried out at 70° C. for 2 hr. After that the reaction liquid was put into 100 ml of iced water to precipitate the reaction product. The precipitate was separated by filtration and put into 40 ml of water containing 2.0 g of $K_2CO_3$, and stirring was made for 30 min. After that an undissolved portion of the precipitate was separated by filtration and dried to thereby obtain 2.6 g of 4-TFM-3-NBA. The mother liquor was rendered acidic by addition of 10 g of hydrochloric acid, and a resultant precipitate was recovered by filtration and refined by recrystallization using 200 ml of water. As the result 5.4 g of 4-TFM-2-NBA was obtained. The total yield of 4-TFM-2-NBA and 4-TFM-3-NBA was 70.4%. Analysis of 4-TFM-3-NBA obtained in this example gave the same results as in Example 1.

What is claimed is:

1. A method of preparing 4-trifluoromethyl-2-nitrobenzoic acid and 4-trifluoromethyl-3-nitrobenzoic acid, comprising the steps of:

nitrating a benzotrifluoride derivative represented by the general formula (1),

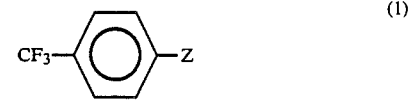

wherein Z represents COY or CY$_3$, and Y represents a halogen atom, with a nitrating agent comprising nitric acid and simultaneously hydrolyzing the radical Z of said benzotrifluoride derivative to thereby obtain a mixture comprising 4-trifluormethyl-2-nitrobenzoic acid and 4-trifluoro-methyl-3-nitrobenzoic acid;

treating said mixture with a basic neutralizing agent so as to obtain a solution containing 4-trifluoromethyl-2-nitrobenzoic acid and a precipitate containing 4-trifluoromethyl-3-nitrobenzoic acid; and isolating 4-trifluoromethyl-2-nitrobenzoic acid from said solution and 4-trifluoromethyl-3-nitrobenzoic acid from said precipitate.

2. A method according to claim 1, wherein the reaction of said benzotrifluoride derivative with said nitrating agent is carried out at a temperature in the range from room temperature to about 150° C.

3. A method according to claim 2, wherein said temperature is in the range from 40 to 100° C.

4. A method according to claim 1, wherein said nitrating agent further comprises sulfuric acid.

5. A method according to claim 1, wherein the radical Z in the general formula is selected from the group consisting of —COCl, —COBr and —CCl$_3$.

6. A method according to claim 1, wherein said neutralizing agent is an inorganic salt of an alkali metal.

7. A method according to claim 1, wherein said neutralzing agent is an inorganic salt of an alkaline earth metal.

* * * * *

UNITED STATES PATENT AND TRADEMARK OFFICE
CERTIFICATE OF CORRECTION

PATENT NO. : 4,845,279
DATED : July 4, 1989
INVENTOR(S) : Yasunobu NISHIMURA et al.

It is certified that error appears in the above-identified patent and that said Letters Patent is hereby corrected as shown below:

On the title page at block [75]: please change the first inventor's name from "Yasunori Nishimura" to --Yasunobu Nishimura et al.--.

Signed and Sealed this

Twenty-second Day of May, 1990

Attest:

HARRY F. MANBECK, JR.

*Attesting Officer*      *Commissioner of Patents and Trademarks*